United States Patent [19]

Osberghaus et al.

[11] 4,032,630

[45] June 28, 1977

[54] SKIN TREATING AGENT CONTAINING POLYHYDROXYPOLYCARBOXYLATE POLYMERS AND PROCESS

[75] Inventors: Rainer Osberghaus, Dusseldorf-Urdenbach; Wilfried Umbach, Langenfeld; Christian Gloxhuber, Haan; Siegfried Braig, Hilden, all of Germany

[73] Assignee: Henkel & Cie G.m.b.H., Dusseldorf-Holthausen, Germany

[22] Filed: Jan. 28, 1975

[21] Appl. No.: 544,813

[30] Foreign Application Priority Data

Jan. 29, 1974 Germany .......................... 2404046

[52] U.S. Cl. .................................. 424/81; 424/59; 424/60; 424/73; 424/172; 424/195; 424/357
[51] Int. Cl.² ........................................ A61K 31/78
[58] Field of Search ................................ 424/81, 78

[56] References Cited

UNITED STATES PATENTS

| | | | |
|---|---|---|---|
| 3,141,864 | 7/1964 | Rink | 260/67 UA |
| 3,142,661 | 7/1964 | Brendlein et al. | 260/67 UA |
| 3,405,095 | 10/1968 | Hartel et al. | 260/67 UA |
| 3,697,643 | 10/1972 | Shepherd et al. | 424/81 X |
| 3,825,498 | 7/1974 | Altenschopler et al. | 260/67 UA |

FOREIGN PATENTS OR APPLICATIONS 1,110,240  4/1968  United Kingdom ................ 424/81

*Primary Examiner*—Dale R. Ore
*Attorney, Agent, or Firm*—Hammond & Littell

[57] ABSTRACT

The present invention relates to compositions for the treatment of the skin containing up to 25% by weight of at least one polymer having carboxyl or carboxylate groups and hydroxyl groups of chiefly rectilinear or cross-linked C—C compounds, the ratio of carboxyl or carboxylate groups to hydroxyl groups in said polymer being in excess of 0.5:1, and particularly between 1.1:1 and 16:1, preferably between 2:1 and 9:1, and the polymerization degree being at least 3, preferably 3 to 300; as well as the method of skin treatment.

13 Claims, 2 Drawing Figures

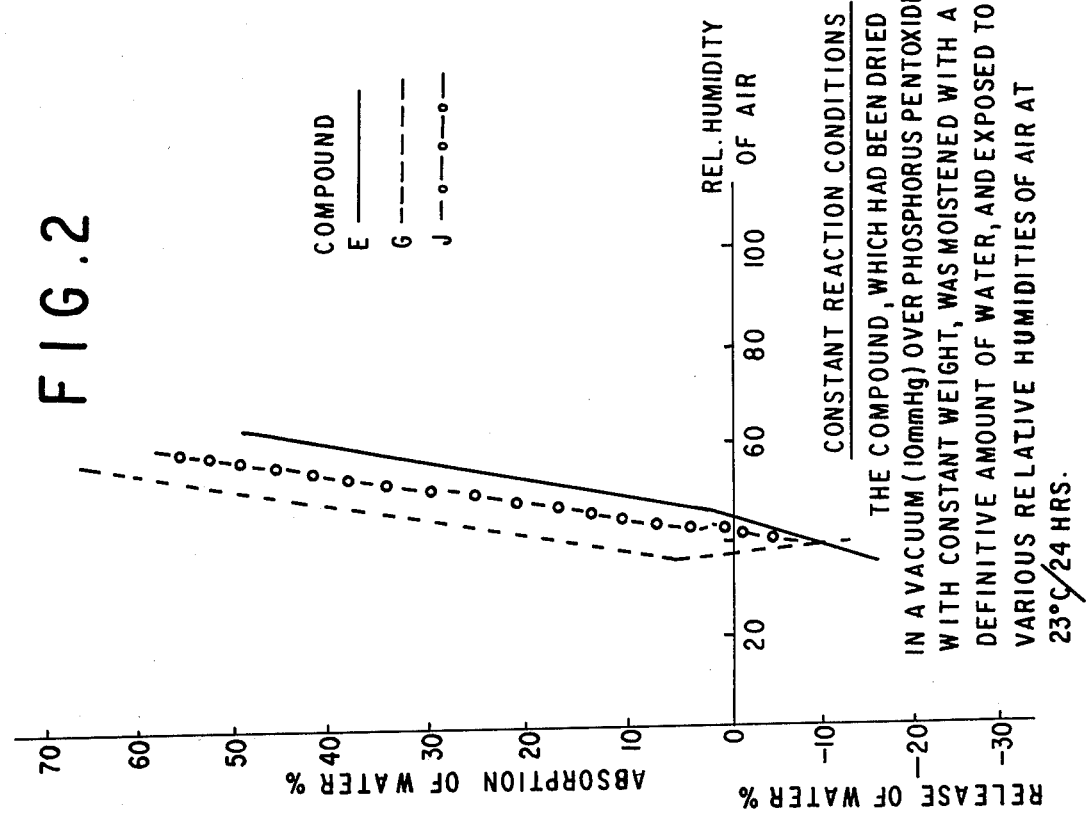
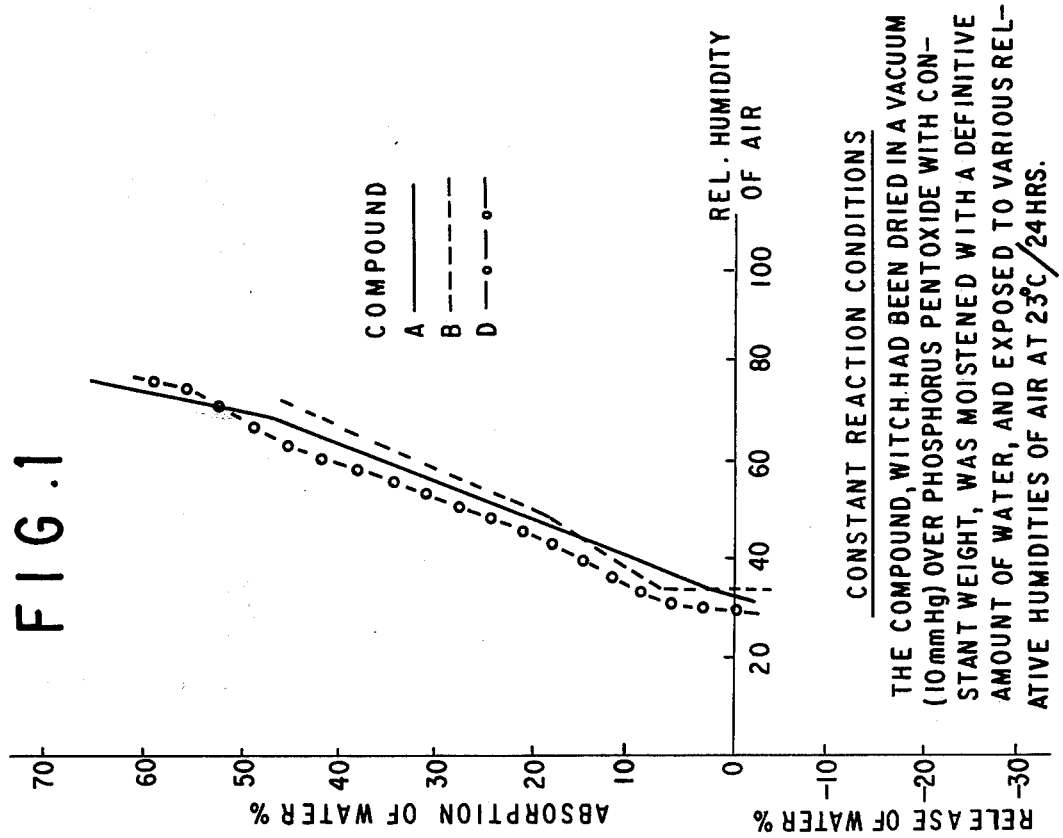

SKIN TREATING AGENT CONTAINING POLYHYDROXYPOLYCARBOXYLATE POLYMERS AND PROCESS

It is generally known that protective measures for healthy skin include, among other things, that the skin surface maintains a certain hygroscopicity. If the substances, on which this hygroscopicity and its constant restoration depend, are removed from the skin by environmental influences, such as repeated washing with substances which have a strong wetting and extracting effect, and the influences of chemicals or severe weather, alterations are produced in the horny layer which can greatly reduce the protective action of the skin against harmful environmental influences.

The object of the present invention is to provide a skin care or skin protection agent, by means of which the functional capacity of the skin may be maintained or increased in spite of harmful environmental influences, and which effectively support the restoration of the horny layer, should any damage have been incurred.

Another object of the present invention is the development of a cosmetic composition for the care and protection of the skin of warm-blooded animals consisting essentially of from 1 to 20% by weight of at least one polyhydroxypolycarboxyl polymer having a polymer chain containing from 55 to 100% of first units selected from the group consisting of

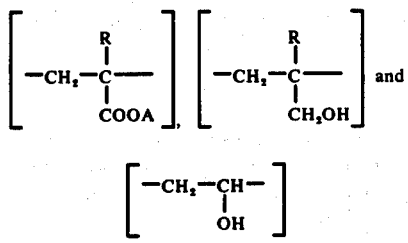

and from 0 to 45% of second units selected from the group consisting of

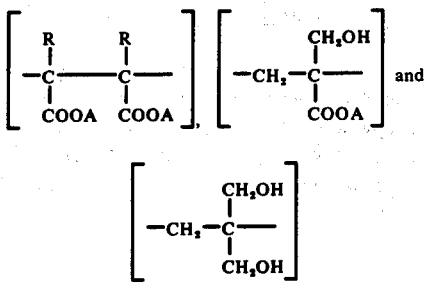

wherein A is a member selected from the group consisting of hydrogen, alkali metal ammonium, lower alkyl ammonium and lower alkylolammonium and R is a member selected from the group consisting of hydrogen and alkyl having from 1 to 6 carbon atoms, said units being present in any order in said polymer chain, said polyhydroxypolycarboxyl polymer having a ratio of —COOA groups to —OH groups of from 0.5:1 to 16:1 and a degree of polymerization of from 3 to 200; and the remainder inert cosmetic excipients.

A further object of the invention is the development of a process for the care and protection of the skin of warm-blooded animals comprising topically applying to the skin a safe but effective amount of the above composition.

These and other objects of the present invention will become more apparent as the description thereof proceeds.

FIGS. 1 and 2 are curves of the equilibrium dampness of various polyhydroxypolycarboxyl polymers according to the invention.

The above objects have been achieved by the discovery of a skin care or skin protection agent comprising conventional constituents such as emulsifiers, fatty substances, plant extracts, solvents, scents, thickeners, and preservatives, and from 1 to 20% by weight, preferably 3 to 10% by weight, based on the weight of the whole agent of at least one polyhydroxypolycarboxyl polymer having a polymer chain containing carboxyl or carboxylate groups and hydroxyl groups and chiefly containing rectilinear or cross-linked C—C compounds, the ratio of carboxyl or carboxylate groups to hydroxyl groups in said polymers exceeding 0.5:1, particularly being between 1.1:1 and 16:1, preferably between 2:1 and 9:1 and the minimum degree of polymerization being 3, with a range of preferably 3 to 300.

The polymers to be used in accordance with the invention are predominantly built up from units of the general formulae

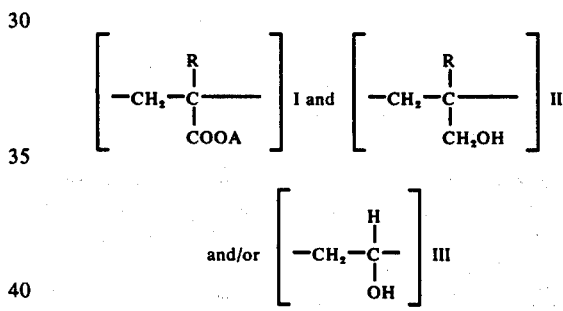

and, optionally, in certain cases also have a subordinate number of units of the general formulae

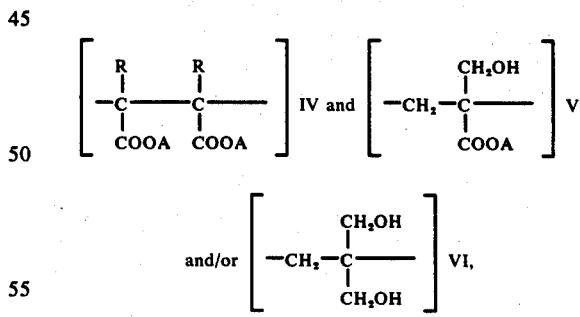

wherein A represents hydrogen, a valence of a mono- or polyvalent metal, particularly an alkali metal, preferably sodium or an ammonium or amine or alkanolamine, and R represents an alkyl group having 1 to 6 carbon atoms, in particular a methyl group, or preferably a hydrogen atom, wherein the units I to VI can be disposed in any sequence desired, and the average frequency of these units corresponds to a ratio of carboxyl or carboxylate groups to hydroxyl groups, which exceeds 0.5:1 and is particularly between 1.1:1 and 16:1, and preferably between 2:1 and 9:1.

More particularly, the present invention relates to a cosmetic composition for the care and protection of the skin of warm-blooded animals consisting essentially of from 1 to 20% by weight of at least one polyhydroxypolycarboxyl polymer having a polymer chain containing from 55 to 100% of first units selected from the group consisting of

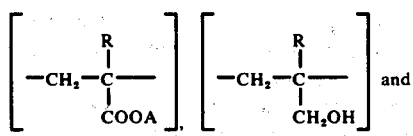

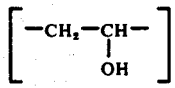

and from 0 to 45% of second units selected from the group consisting of

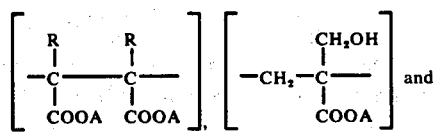

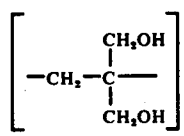

wherein A is a member selected from the group consisting of hydrogen, alkali metal ammonium, lower alkyl ammonium and lower alkylolammonium and R is a member selected from the group consisting of hydrogen and alkyl having from 1 to 6 carbon atoms, said units being present in any order in said polymer chain, said polyhydroxypolycarboxyl polymer having a ratio of —COOA groups to —OH groups of from 0.5:1 to 16:1 and a degree of polymerization of from 3 to 200, and the remainder inert cosmetic excipients; as well as a process for the care and protection of the skin of warm-blooded animals comprising topically applying to the skin a safe but effective amount of the above composition.

The polymers to be used in accordance with the invention are extremely suitable for maintaining or restoring the water retention of the skin and thus for keeping the skin soft, supple and fully capable of performing its function.

The production of these polyhydroxypolycarboxyl polymers is preferably effected by the oxidative homopolymerization of acrolein or by the oxidative copolymerization of acrolein, and acrylic acid or alkenoic acids having 3 to 8 carbon atoms and subsequent treatment of the polymer with a strong base, such as an alkali metal hydroxide in accordance with the Cannizzaro reaction, as described in the German Published Application DOS 1,904,940. Alternatively, the treatment with the strong base can also be effected with simultaneous formaldehyde condensation. Polymers are then obtained which, in addition to the units I to IV, also contain subordinate quantities of units V and VI. However, in each case the polymerization conditions and reaction conditions, and in particular the quantities of the oxidation agent, must be such that the required ratio of carboxyl or carboxylate groups to the hydroxyl groups in the end product and the minimum degree of polymerization of 3 are obtained, i.e., an appropriate number of units I or units I and IV must be present at the same time.

Peroxides or peracids, but preferably hydrogen peroxide, are used as oxidation agents. The carboxyl group content in the polymer can, on the one hand, be influenced by the ratio of the oxidation agent amount to the acrolein amount, and on the other hand by the utilization of acrylic acid as comonomer. The greater the ratio of the oxidation agent amount to the acrolein amount, the greater the number of carboxyl groups present in the polymer, and vice versa. Since the peroxy compound simultaneously acts as a regulator, the degree of polymerization is influenced by the amount of this compound which is used, and the polymerization degree decreases as the amount of oxidation agent increases. On the other hand, the degree of polymerization can be influenced by the utilization of acrylic acid as comonomer and increases as the content of acrylic acid in the comonomer mixture rises.

The homopolymerization of acrolein or the copolymerization of acrolein and acrylic acid can be carried out independently of the desired carboxyl group content in the polymer, either by solution polymerization or precipitation polymerization, preferably in an aqueous medium. The polyaldehydocarboxylic acids which are obtained in this manner and have the following type of formula, i.e., without information with regard to the sequence of the units of the formula and without consideration of proportions of any acrolein copolymers which may be present.

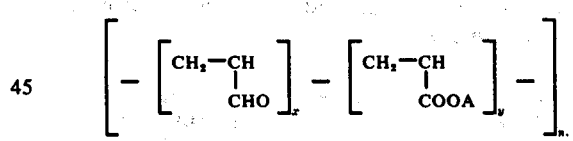

This polymer can be further reacted in aqueous solution or suspension in a manner known per se with a strong base, possibly in the presence of formaldehyde. Thus, polyhydroxycarboxylates of the following formula structure

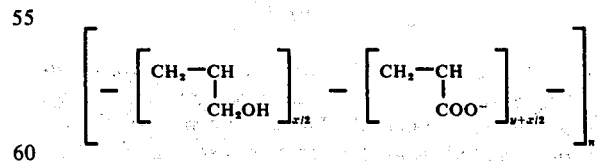

are produced by means of the Cannizzaro reaction. If the Cannizzaro reaction of the polyaldehydrocarboxylic acids is carried out in the presence of formaldehyde, then in the theoretical borderline case of complete aldol condensation, followed by complete Cannizzaro reaction, polyhydroxycarboxylates are obtained which can formally be described in the following manner:

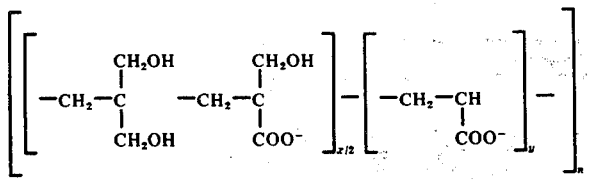

In the above formulae $x$ represents basic/molar % CHO/100[*]
$y$ represents basic/molar % COO⁻/100[*]
$n$ represents polymerization degree

[*]Basic/molar % represent basic/molar percentages according to Trommsdorff (Inaugural diss. Freiburg i. Br. 1931).

In a solution reaction, solutions of the salts of the polyhydroxypolycarboxylic acids, together with an excess of liquor, are obtained. The neutralization of the solution is advantageously carried out with the polyhydroxypolycarboxylic acids themselves in pure solid form, so that pure neutral solutions of the salts of the polyhydroxypolycarboxylic acids are obtained, from which said salts of the polyhydroxypolycarboxylic acids can easily be isolated by evaporation of the water. It is also possible to control the course of the Cannizzaro reaction in such a manner that practically neutral salt solutions are finally obtained, in that the amount of liquor added is apportioned so that as the reaction degree increases as the amount of excess liquor decreases and finally reaches zero at the end of the reaction.

The polymers which are to be used in accordance with the invention chiefly have C—C links in the main chain and can be both rectilinear and cross-linked. When acrolein is used, possibly together with acrylic acid as starting monomers, polymers are obtained which are predominantly built up from the above-mentioned units I and II or III. If other comonomers are used in addition to acrolein and possibly acrylic acid or other alkenoic acids of the acrylic acid series, e.g., maleic acid and/or vinyl alcohol derivatives and/or allylalcohol, the units III and IV are present in the polymers in subordinate number in the main chain. The other monomers are employed in lower amounts of from 0 to 45% of the monomer mixture. If the reaction of the polyaldehydocarboxylic acids with a strong base is carried out in accordance with the Cannizzaro reaction in the presence of formaldehyde, the units V and VI are formed.

The polymers to be used in accordance with the invention are colorless, odorless and completely stable, and possess excellent physiological compatability and have no disadvantageous effects on the skin care and skin protection agents in which they are mixed.

It is known that in addition to other factors a certain hygroscopicity is necessary for the protection of a healthy skin. If the skin is deprived of the substances which are responsible for this hygroscopicity as well as its continual restoration by environmental circumstances such as repeated washings, effect of chemicals or strong weather influences, alterations occur in the stratum corneum, as a result of which the protective effect of the skin against harmful influences of the environment may be considerably diminished.

It was found that the functional capacity of the skin may be maintained or restored even to a higher degree than before if it is treated with agents for the care and protection of the skin, which besides the customary constituents include from 1 to 20% by weight, preferably 3 to 10% by weight, based on the total composition of the polyhydroxypolycarboxyl polymers in accordance with the invention.

Among the compositions for the care and protection of the skin having special skin-caring properties due to the addition of the polyhydroxypolycarboxyl polymers in accordance with the invention are emulsions of oil-in-water or water-in-oil type. These are the conventional day creams, baby creams, night creams and nourishing creams, cleansing creams, skin protection creams, glycerol creams, creams with special additives of animal or vegetable origin, sun protection or sun tanning creams, and sun protection emulsions, face lotions and after-shave lotions. The incorporation of the agents for care and protection of the skin may take place in the known manner by simple stirring-in or dissolving. In addition to the polyhydroxypolycarboxyl polymers in accordance with the invention, the cosmetic preparations may contain the constituents normally present in them such as emulsifiers, fatty substances, plant extracts, preservatives, perfumes, solvents, thickeners and preservatives in the customary amounts. The pH value of the agents for the care and protection of the skin may be in the acid to neutral region (pH 5 – 7.0) and is approximately adjusted to weakly acid values of about pH 6.

The following examples are intended to illustrate the subject of the invention without, however, limiting it to these examples.

EXAMPLES

Several polymers having carboxyl or carboxylate and hydroxyl groups are to be mentioned first of all, which can be used as skin moisturizing agents in the skin care and skin protection agents according to the invention.

Product A: Poly-(hydroxycarboxylic acid)-sodium salt, oxidative copolymer of acrolein and acrylic acid, reacted according to Cannizzaro, medium polymerization degree of approximately 10.

430 ml of a mixture of 92% water, 7% acrylic acid and 1% acrolein was placed together with 400 ml of 30% hydrogen peroxide solution in a reactor. During stirring and heating from 55° C to 60° C, 365 ml of freshly distilled acrolein was added to the reaction mixture dropwise within approximately five hours. When all the acrolein had been added, the mixture was briefly heated to about 80° C. Thereafter, the mixture was cooled, reduced to approximately half its volume under vacuum and was immediately processed further as the solution of a polyaldehydocarboxylic acid with a COOH content of 80%, a C=O content of 20% and a medium polymerization degree of 10.

200 ml of the polyaldehydocarboxylic acid solution, which was produced as previously described, was mixed with 272 ml of distilled water. 175 ml of 40% sodium hydroxide solution was then added dropwise during stirring over 1½ hours. After standing for several hours an alkaline solution of the salt of the appropriate polyhydroxypolycarboxylic acid is obtained. The excess sodium hydroxide can be neutralized by adding a corresponding quantity of the appropriate polyhydroxypolycarboxylic acid or mineral acid, such as hydrochloric acid. In certain cases, the solid product can be obtained from the solution by evaporation of the water, but in the majority of cases the aqueous solutions can be used as they are without further processing.

The other products, which are given hereinafter in Table 1, were produced in corresponding manner.

TABLE I

Data for the polyhydroxypolycarboxylic acids tested

| Product | Chemical Specification | n Average polymerization degree | Average molecular weight | COO content (bas./mol %) | OH content (bas./mol %)[1] |
|---------|------------------------|-------------------------------|-------------------------|--------------------------|----------------------------|
| B | Poly(hydroxycarboxylic acid)-sodium salt; "oxidative" copolymer of acrolein and acrylic acid, reacted according to Cannizzaro. | 15–25 | 1300–2300 | 75–85 | 15–25 |
| C | Poly(hydroxycarboxylic acid)-sodium salt; "oxidative" copolymer of acrolein and acrylic acid, reacted according to Cannizzaro with formaldehyde condensation. | ca. 20 | 1400–2500 | 75–85 | 15–25 |
| D | Poly(hydroxycarboxylic acid)-sodium salt; "oxidative" copolymer of 65 mol % acrolein and 35 mol % acrylic acid, reacted according to Cannizzaro. | 15–30 | 1350–2700 | 75–85 | 20–30 |
| E | Poly(hydroxycarboxylic acid)—sodium salt; "oxidative" copolymer of 65 mol % acrolein and 35 mol % acrylic acid, reacted according to Cannizzaro with formaldehyde condensation. | 15–30 | 1400–3000 | 75–85 | 20–35 |
| F | Poly(hydroxycarboxylic acid)—sodium salt; "oxidative" copolymer of 57 mol % acrolein and 43 mol % acrylic acid, reacted according to Cannizzaro. | 30–50 | 2700–4500 | 75–85 | 20–30 |
| G | Poly(hydroxycarboxylic acid)—sodium salt; "oxidative" copolymer of 57 mol % acrolein and 43 mol % acrylic acid, reacted according to Cannizzaro with formaldehyde condensation. | 30–50 | 2800–4800 | 75–85 | 23–35 |
| H | Poly(hydroxycarboxylic acid)-sodium salt; "oxidative" copolymer of 50 mol % acrolein and 50 mol % acrylic acid, reacted according to Cannizzaro. | 50–70 | 4500–6500 | 85–90 | 10–20 |
| J | Poly(hydroxycarboxylic acid)-sodium salt; "oxidative" copolymer of 50 mol % acrolein and 50 mol % acrylic acid, reacted according to Cannizzaro with formaldehyde condensation. | 50–70 | 4600–7000 | 85–90 | 20–40 |

[1]-Functional groups per 100 monomer units in the molecule chain.

The favorable action of the compounds, which are to be used in accordance with the invention with regard to capacity for the absorption and retention of water, was also determined by means of test methods which are described more fully hereinafter. A process for determining the equilibrium dampness, which constitutes a gauge for the water retention capacity, and the determination of the water retention, rehydration and elasticity of impregnated pig epidermis is described in these tests.

1. Determination of the equilibrium dampness

The substances (about 300 to 500 mg) to be tested were moistened with a defined quantity of water and exposed for 24 hours at 23° C to various relative atmospheric humidities (1, 30, 47, 65, 89 and 100% relative humidity). The amount of water absorbed or desorbed was determined gravimetrically and plotted on a graph. The relative humidity at which neither expulsion nor retention of water is effected, can be determined from the resultant curves. (FIGS. 1 and 2). This value, which is designated as the equilibrium dampness, is a gauge for the water retention capacity of a substance. The lower the value, the more positive should be the assessment of the product. The steepness of the curve, in addition, indicated the water retaining capacity (hygroscopicity) of the substance.

The values are reported in Table II.

2. Tests on the pig epidermis a. To obtain the pig epidermis

As soon as the pigs have been killed, the bristles of the skin are cut off by means of a shearing machine (shearing head of 0.1 mm). The pigs are soaked for 3 to 5 minutes in warm water of 60° C, the epidermis is then peeled off and stored at −20° C until used.

b. Determination of the water retention and the rehydration of impregnated pig epidermis.

Stamped out pieces of epidermis (1 × 2 cm) were soaked for 2 hours in a 10% solution of the test substance, excess moisture was removed by means of a small press under standardized conditions and the pieces were dried for 24 hours, hanging free between 2 clamps in a 100 ml Erlenmeyer flask at 23° C both at 30% relative humidity and 50% relative humidity (set by sulfuric acid/water mixtures). The drying out of the impregnated test pieces to X% of the initial weight was compared with the corresponding value of the epidermis which had been soaked only in water (blank value). In Table II, the improvement in the water retention and the rehydration as compared with the blank value is given in Δ% of H₂O. The deviations in each double test amounted to a maximum of ± 2 absolute units. If greater deviations occurred, the test was repeated. The rehydration was determined analogously by drying the pig epidermis, which had been impregnated and from which the excess moisture had been removed, for 24 hours at 30% relative humidity, and by subsequent 24-hour incubation at 90% relative humidity.

c. Gauging of elasticity of impregnated pig epidermis

Stamped out pieces of pig epidermis (1 × 6 cm) were soaked for 2 hours in a 10% aqueous solution of the substance which was to be tested, and excess moisture was removed from these pieces under standardized conditions. The test pieces were incubated for 24 hours, hanging free between 2 clamps both at 75% relative humidity and at 90% relative humidity and were stretched in a nipping tensile-testing machine (type: 1402) with 0 to 50 pund loading. The amount of stretch, which was measured in the Hooke range with loadings of 5 to 30 pund, was given in mm as a gauge for the elasticity.

The measured values obtained in the tests described above can be seen hereinafter in Table II and also from the enclosed graphs, FIG. 1 showing the water retention of polymers A, B and D, and FIG. 2 showing the water retention of polymers E, G and J.

In the graphs the constant conditions were as follows: The polymer was dried in a vacuum (10 torr) over phosphorus pentoxide to a constant weight, was moistened with a defined quantity of water and was exposed for 24 hours at 23° C to various relative atmospheric humidities.

These afore-mentioned measured values of Table II, as well as the graphs of FIGS. 1 and 2, also confirm the suitability of the products which are to be used in accordance with the invention as skin moisture-containing agents in skin care and skin protection agents. The equilibrium dampness figures show that none of the products expel water until very low relative humidities have been reached. Even at low relative humidities of ≥ 46%, the products absorb moisture from the surrounding atmosphere.

In the following, we will give a few examples of cosmetic preparations containing substances in accordance with the invention of skin humectants.

EXAMPLE 1

| Day cream, slightly greasy | Parts by weight |
|---|---|
| Fatty acid partial glyceride Cutina MD® Dehydag | 6.0 |
| Stearic acid | 8.0 |

EXAMPLE 1-continued

| Day cream, slightly greasy | Parts by weight |
|---|---|
| Mixture of nonionic emulsifiers Emulgin C 700® Dehydag | 3.0 |
| 2-octyl-dodecanol | 4.0 |
| Vegetable oil | 3.0 |
| Paraffin oil | 5.0 |
| Triethanolamine | 0.4 |
| 1,2-propylene glycol | 3.0 |
| Product A | 3.0 |
| Nipagin M | 0.2 |
| Perfume oil | 1.0 |
| Water | 63.4 |

EXAMPLE 2

| Baby cream | Parts by Weight |
|---|---|
| Mixture of higher molecular esters, mainly mixed esters of pentaerythritol fatty acid ester and critic acid fatty alcohol ester Dehymuls E® Dehydag | 7.0 |
| Decyl oleate | 10.0 |
| Vaseline | 10.0 |
| Wool fat | 5.0 |
| Boric acid | 0.2 |
| Talcum | 12.0 |
| Zinc oxide | 8.0 |
| Nipagin M | 0.2 |
| Product C | 5.0 |
| Water | 42.6 |

TABLE II

Equilibrium dampness and measured values for pig epidermis

| | | Measurements from the pig epidermis | | | | |
|---|---|---|---|---|---|---|
| | Equilibrium dampness | Water Retention Δ% H₂O after drying out | | Rehydration Δ% water absorption | mm stretch with between 5 and 30 pund loading | |
| Product | (% r.h.) | at 30% r.h. | at 50% r.h. | at 90% r.h. | at 90% r.h. | at 75% r.h. |
| Blank value | — | 0 | 0 | 0 | 0.3–0.5 | 0 |
| A | 35 | 29 | 37 | 67 | 3.0 | 0.9 |
| C | 39 | 32 | 26 | 71 | 2.5 | 1.3 |
| D | 35 | 24 | 19 | 48 | 1.8 | 0.8 |
| E | 45 | 13 | 28 | 60 | 2.3 | 0.6 |
| F | 45 | 27 | 19 | 49 | 2.6 | 0.8 |
| H | 44 | 18 | 6 | 37 | 1.0 | 0.8 |
| B | 36 | 34 | 32 | 63 | 2.9 | 1.0 |
| G | 42 | 20 | 21 | 58 | 2.4 | 0.7 |
| J | 45 | 15 | 9 | 34 | 1.7 | 0.6 |

EXAMPLE 3

| Night cream | Parts by Weight |
|---|---|
| Colloidally dispersed mixture of 90 parts of cetyl-stearyl alcohol and 10 parts of sodium lauryl sulfate | 10.0 |
| 2-Octyl-dodecanol | 12.0 |
| Vegetable oil | 7.0 |
| Wool fat | 2.0 |
| Glycerol | 1.0 |
| Product E | 5.0 |
| Nipagin M | 0.2 |
| Perfume Oil | 1.0 |
| Water | 61.8 |

EXAMPLE 4

| Boro-glycerol cream | Parts by Weight |
|---|---|
| Colloidally dispersed mixture of 90 parts of cetyl-stearyl alcohol and 10 parts of sodium lauryl sulfate | 12.0 |
| 2-Octyl-dodecanol | 8.0 |
| Vegetable oil | 5.0 |
| Boric acid | 2.0 |
| Glycerol | 28.0 |
| Nipagin M | 0.2 |
| Product B | 3.0 |
| Water | 41.8 |

EXAMPLE 5

| Sun protection cream | Parts by Weight |
|---|---|
| Mixture of higher molecular esters with fatty substances Dehymuls K® Dehydag | 30.0 |
| Decyl oleate | 15.0 |
| Light protection agent | 5.0 |
| Nipagin M | 0.2 |
| Product G | 3.0 |
| Water | 46.8 |

EXAMPLE 6

| Face mask | Parts by Weight |
|---|---|
| Mixtures of fatty acid partial glyceride with emulsifiers Cutina Le® Dehydag | 12.0 |
| Decyl oleate | 4.0 |
| Vitamin oil | 5.0 |
| Kaolin | 2.0 |
| Rice starch | 3.0 |
| Nipagin M | 0.2 |
| Product F | 6.0 |
| Water | 67.8 |

EXAMPLE 7

| After-shave lotion | Parts by Weight |
|---|---|
| Oleyl/cetyl alcohol | 1.0 |
| Ethanol 96% | 67.5 |
| Menthol | 0.2 |
| Camphor | 0.2 |
| Peru balsam | 0.1 |
| Perfume | 0.5 |
| Hamamelis extract | 10.0 |
| Boric acid | 0.5 |
| Product D | 10.0 |
| Water | 10.0 |

EXAMPLE 8

| Face lotion | Parts by Weight |
|---|---|
| Cucumber essence | 15.0 |
| Citric acid | 0.2 |
| Ethanol 96% | 15.0 |
| Product C | 10.0 |
| Perfume | 1.0 |
| Water | 58.8 |

In place of the compounds in accordance with the invention mentioned in the above examples, others of the products in accordance with the invention may be used with equally good success.

The preceding specific embodiments are illustrative of the practice of the invention. It is to be understood, however, that other expedients known to those skilled in the art, or given herein, may be employed without departing from the spirit of the invention or the scope of the appended claims.

We claim:

1. A cosmetic moisturizing composition for the care and protection of the skin of warm-blooded animals consisting essentially of an emulsion adjusted to a pH between 5 and 7 containing an emulsifier, from 1 to 20% by weight of at least one polyhydroxypolycarboxyl polymer having a polymer chain containing from 55 to 100% of first units selected from the group consisting of

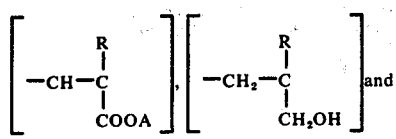

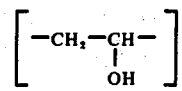

and from 0 to 45% of second units selected from the group consisting of

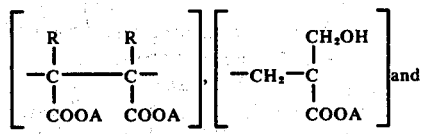

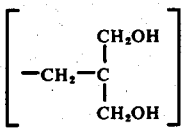

wherein A is a member selected from the group consisting of hydrogen, alkali metal, ammonium, lower alkyl ammonium and lower alkylolammonium and R is a member selected from the group consisting of hydrogen and alkyl having from 1 to 6 carbon atoms, said units being present in any order in said polymer chain, said polyhydroxypolycarboxyl polymer having a ratio of —COOA groups to —OH groups of from 0.5:1 to 16:1 and a degree of polymerization of from 3 to 200; and the remainder inert cosmetic excipients, said emulsion being selected from the group consisting of oil-in-water emulsions and water-in-oil emulsions.

2. The composition of claim 1 wherein said at least one polyhydroxypolycarboxyl polymer is present in an amount of from 3 to 10% by weight.

3. The composition of claim 1 wherein R is hydrogen.

4. The composition of claim 3 wherein A is sodium.

5. The composition of claim 1 wherein said ratio of —COOA groups to —OH groups is from 2:1 to 9:1 and said degree of polymerization is from 3 to 100.

6. The composition of claim 1 wherein substantially all of the units in said polymer chain are said first units.

7. The composition of claim 1 wherein the pH is 6.

8. A cosmetic moisturizing composition consisting essentially of a water and ethanal solution adjusted to a pH between 5 and 7 containing from 1 to 20% by weight of at least one polyhydroxypolycarboxyl polymer having a polymer chain containing from 55 to 100% of first units selected from the group consisting of

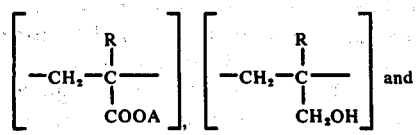

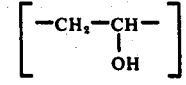

and from 0 to 45% of second units selected from the group consisting of

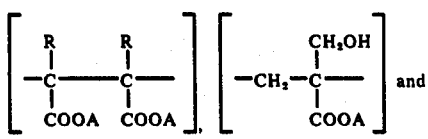

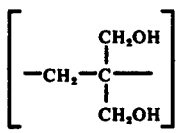

wherein A is a member selected from the group consisting of hydrogen, alkali metal, ammonium, lower alkyl ammonium and lower alkylolammonium and R is a member selected from the group consisting of hydrogen and alkyl having from 1 to 6 carbon atoms, said units being present in any order in said polymer chain, said polyhydroxypolycarboxyl polymer having a ratio of —COOA groups to —OH groups of from 0.5:1 to 16:1 and a degree of polymerization of from 3 to 200; and the remainder inert cosmetic excipients.

9. A process for the care and protection of the skin of warm-blooded animals comprising topically applying to the skin a safe but effective amount as a moisturizing agent of a cosmetic moisturizing composition consisting essentially of an emulsion adjusted to a pH between 5 and 7 containing an emulsifier, from 1 to 20% by weight of at least one polyhydroxypolycarboxyl polymer having a polymer chain containing from 55 to 100% of first units selected from the group consisting of

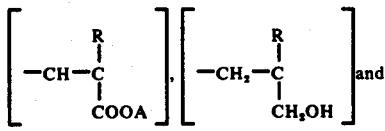

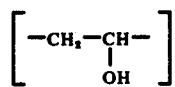

and from 0 to 45% of second units selected from the group consisting of

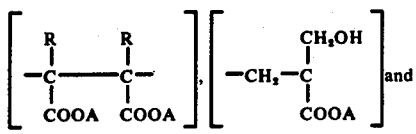

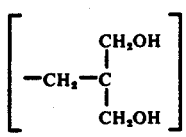

wherein A is a member selected from the group consisting of hydrogen, alkali metal, ammonium, lower alkyl ammonium and lower alkylolammonium and R is a member selected from the group consisting of hydrogen and alkyl having from 1 to 6 carbon atoms, said units being present in any order in said polymer chain, said polyhydroxypolycarboxyl polymer having a ratio of —COOA groups to —OH groups of from 0.5:1 to 16:1 and a degree of polymerization of from 3 to 200; and the remainder inert cosmetic excipients, said emulsion being selected from the group consisting of oil-in-water emulsions and water-in-oil emulsions.

10. A process for the care and protection of the skin of warm-blooded animals comprising topically applying to the skin a safe but effective amount as a moisturizing agent of a cosmetic moisturizing composition consisting essentially of a water and ethanol solution adjusted to a pH between 5 and 7 containing from 1 to 20% by weight of at least one polyhydroxypolycarboxyl polymer having a polymer chain containing from 55 to 100% of first units selected from the group consisting of

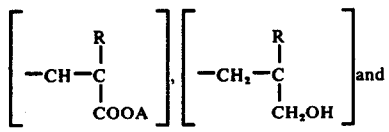

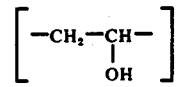

and from 0 to 45% of second units selected from the group consisting of

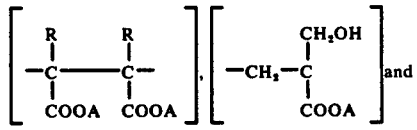

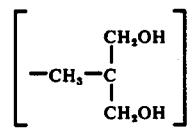

wherein A is a member selected from the group consisting of hydrogen, alkali metal, ammonium, lower alkyl ammonium and lower alkylolammonium and R is a member selected from the group consisting of hydrogen and alkyl having from 1 to 6 carbon atoms, said units being present in any order in said polymer chain, said polyhydroxypolycarboxyl polymer having a ratio of —COOA groups to —OH groups of from 0.5:1 to 16:1 and a degree of polymerization of from 3 to 200; and the remainder inert cosmetic excipients.

11. The process of claim 9 wherein said at least one polyhydroxypolycarboxyl polymer is present in an amount of from 3 to 10% by weight.

12. The process of claim 9 wherein said ratio of —COOA groups to —OH groups is from 2:1 to 9:1 and said degree of polymerization is from 3 to 100.

13. The process of claim 9 wherein substantially all of the units in said polymer chain are said first units.

* * * * *